US012577571B2

(12) United States Patent
Keyel et al.

(10) Patent No.: US 12,577,571 B2
(45) Date of Patent: Mar. 17, 2026

(54) MUTANT DNASE1L3 WITH IMPROVED SERUM HALF-LIFE

(71) Applicant: Texas Tech University System, Lubbock, TX (US)

(72) Inventors: Peter Keyel, Lubbock, TX (US); Roger B. Sutton, Lubbock, TX (US); Jon McCord, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 786 days.

(21) Appl. No.: 17/763,913

(22) PCT Filed: Oct. 1, 2020

(86) PCT No.: PCT/US2020/053735
§ 371 (c)(1),
(2) Date: Mar. 25, 2022

(87) PCT Pub. No.: WO2021/071733
PCT Pub. Date: Apr. 15, 2021

(65) Prior Publication Data
US 2022/0380780 A1      Dec. 1, 2022

Related U.S. Application Data

(60) Provisional application No. 62/911,711, filed on Oct. 7, 2019.

(51) Int. Cl.
| | |
|---|---|
| *C12N 9/16* | (2006.01) |
| *C12N 15/52* | (2006.01) |
| *C12N 15/70* | (2006.01) |
| *C12N 15/81* | (2006.01) |

(52) U.S. Cl.
CPC ............. *C12N 15/52* (2013.01); *C12N 15/70* (2013.01); *C12N 15/815* (2013.01)

(58) Field of Classification Search
CPC .. C12Y 301/21001; C12N 9/16; C12N 15/70; C12N 15/52; C12N 15/815
See application file for complete search history.

(56) References Cited

U.S. PATENT DOCUMENTS

| | | | |
|---|---|---|---|
| 5,766,897 A | 6/1998 | Braxton | |
| 6,482,626 B2 * | 11/2002 | Baker | ...................... C12N 9/22 |
| | | | 435/320.1 |
| 7,067,298 B2 | 6/2006 | Atham et al. | |
| 7,407,785 B2 | 8/2008 | Lazarus et al. | |
| 9,603,907 B2 | 3/2017 | Shaatiel et al. | |

FOREIGN PATENT DOCUMENTS

| | | |
|---|---|---|
| WO | 2015066557 | 5/2015 |
| WO | 2016069889 | 5/2016 |
| WO | 2019036719 A2 | 2/2019 |

OTHER PUBLICATIONS

Extended European Search Report, EP 20874456.5 dated Aug. 2, 2023.
Dozier, Jonathan et al., "Site-Specific PEGylation of Therapeutic Proteins", International Journal of Molecular Sciences, vol. 16, No. 11, Oct. 28, 2015 (Oct. 28, 2015), pp. 25831-25864.
McCord, Jon J et al., "Structural Investigations into the Serum EndonucleaseDnase1L3, as it Relates to Systemic Lupus Erythematous",Biophysical Journal, vol. 116, No. 3, Suppl. 1, Feb. 15, 2019 (Feb. 15, 2019), p. 474A.
Abuchowski, A., et al. "Effect of covalent attachment of polyethylene glycol on immunogenicity and circulating life of bovine liver catalase." Journal of Biological Chemistry (1977) 252(11):3582-3586.
International Search Report and Written Opinion for PCT/US2020/053735 dated Feb. 19, 2021.
Napirei, Markus, et al. "Murine serum nucleases—contrasting effects of plasmin and heparin on the activities of Dnase1 and Dnase1-like 3 (Dnase1I3)." The FEBS Journal (2009), 276(4):1059-1073.
Sisirak, Vanja, et al. "Digestion of chromatin in apoptotic cell microparticles prevents autoimmunity." Cell (2016), 166(1): 88-101.
Wilber, A., et al., "Deoxyribonuclease I-like III is an inducible macrophage barrier to liposomal transfection." Molecular Therapy (2002), 6(1):35-42.

* cited by examiner

*Primary Examiner* — Maryam Monshipouri
(74) *Attorney, Agent, or Firm* — Edwin S. Flores; Daniel J. Chalker; Chalker Flores, LLP

(57) ABSTRACT

The present invention includes a mutant Dnase1LS having at least about a 95% identity with a nucleic acid sequence encoding the protein of SEQ ID NO: 2-8 for a mutant Dnase1LS comprising at least one mutation for post-translational modification or attachment of a molecule to the mutant Dnase1LS to increase the serum half-life of the mutant Dnase1LS, nucleic acids encoding the same, host cells, and methods of making the mutant Dnase1LS.

13 Claims, 6 Drawing Sheets

Specification includes a Sequence Listing.

MUTANT DNASE1L3 WITH IMPROVED SERUM HALF-LIFE

CROSS-REFERENCE TO RELATED APPLICATIONS

This application is the National Stage of International Application No. PCT/US2020/053735, filed on Oct. 1, 2020 claiming the priority to U.S. Provisional Application Ser. No. 62/911,711, filed Oct. 7, 2019, the entire contents of which are incorporated herein by reference.

TECHNICAL FIELD OF THE INVENTION

The present invention relates in general to the field of DNase I, and more particularly to an improved mutant DNaseIL3.

STATEMENT OF FEDERALLY FUNDED RESEARCH

None.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Sep. 30, 2020, is named TECH2145WO_SeqList.txt and is 22, kilo bytes in size.

BACKGROUND OF THE INVENTION

Without limiting the scope of the invention, its background is described in connection with DNase I proteins.

One such patent is U.S. Pat. No. 9,603,907, issued to Shaaltiel, et al., entitled, "Dry powder formulations of dNase I" and is said to teach DNase I formulations for pulmonary administration and, e.g., a dry powder formulation comprising, as an active ingredient, human DNase I, methods, dry powder inhalation devices and systems for the therapeutic use thereof are provided. Further, a key limitation of Dnase1 is that it poorly digests DNA present as chromatin in apoptotic bodies (see Sisirak et al, Cell 2016 166:1-14, Napirei et al 2009 FEBS J 276:1059-1073, Wilber et al 2002 Mol Ther 6:35-42).

Another such patent is U.S. Pat. No. 7,407,785, issued to Lazarus, entitled "Human DNase I hyperactive variants", which is said to teach amino acid sequence variants of human DNase I that have increased DNA-hydrolytic activity. The invention is said to include nucleic acid sequences encoding such hyperactive variants that enable the production of these variants in quantities sufficient for clinical use, and pharmaceutical compositions and therapeutic uses of hyperactive-variants of human DNase I.

Yet another such patent is U.S. Pat. No. 7,067,298, issued to Latham, et al. entitled, "Compositions and methods of using a synthetic Dnase I" and is said to teach a synthetic bovine DNase I for use in molecular biology applications, including: degradation of contaminating DNA after RNA isolation; RNA clean-up prior to, or in conjunction with, RT-PCR after in vitro transcription; identification of protein binding sequences on DNA (DNase I footprinting); prevention of clumping when handling cultured cells; tissue dissociation and creation of fragmented DNA for in vitro recombination reactions.

What is needed are novel compositions that increase the efficacy and availability of DNase proteins for therapeutic and other uses.

SUMMARY OF THE INVENTION

In one embodiment, the present invention includes an isolated and purified nucleic acid comprising a nucleic acid encoding a mutant Dnase1L3 comprising at least one mutation for post-translational modification or attachment of a molecule to the mutant Dnase1L3 to increase the serum half-life of the mutant Dnase1L3. In one aspect, the nucleic acid further comprising a nucleic acid sequence optimized for microbial expression. In another aspect, the mutant Dnase1L3 comprises the mutant Dnase1L3 comprises at least one of: an S112C mutation, an S131C mutation, or an S279C mutation. In another aspect, the mutant Dnase1L3 further comprises at least one of: an S91C, an S131C or an S253C. In another aspect, the mutant Dnase1L3 comprises the mutant Dnase1L3 comprises at least two mutations selected from S91C, S112C, S131C, and S279C mutation. In another aspect, the nucleic acid further comprises a nucleic acid segment encoding a leader sequence. In another aspect, the nucleic acid comprises a codon-optimized mutant Dnase1L3 nucleic acid encoding SEQ ID NOS: 2-8. In another aspect, the protein encoded by the nucleic acid comprises an about 95 percent identity or higher with a codon-optimized mutant Dnase1L3 of SEQ ID NO: 2-8.

In another embodiment, the present invention includes an expression vector comprising a nucleic acid encoding the protein of SEQ ID NO: 2-8 for a mutant Dnase1L3 operably linked to a promoter recognized by a host cell transformed with the vector. In one aspect, the host cell is a bacterial or yeast cell. In another aspect, the host cell comprises E. coli or Pichia pastoris.

In another embodiment, the present invention includes mutant Dnase1L3 having at least about a 95% identity with a nucleic acid sequence encoding the protein of SEQ ID NO: 2-8 for a mutant Dnase1L3 comprising at least one mutation for post-translational modification or attachment of a molecule to the mutant Dnase1L3 to increase the serum half-life of the mutant Dnase1L3. In one aspect, the mutant Dnase1L3 further comprises a nucleic acid sequence optimized for microbial expression. In one aspect, the mutant Dnase1L3 comprises the mutant Dnase1L3 comprises at least one of: an S91C mutation, an S112C mutation, an S131C mutation, or an S253C mutation. In another aspect, the mutant Dnase1L3 further comprises at least one of: an S131C or an S272C. In another aspect, the mutant Dnase1L3 comprises the mutant Dnase1L3 comprises at least two mutations selected from S91C, S112C, S131C, and S272C mutation. In another aspect, the nucleic acid further comprises a nucleic acid segment encoding a leader sequence. In another aspect, the nucleic acid comprises a codon-optimized mutant Dnase1L3 nucleic acid encoding SEQ ID NOS: 2-8. In another aspect, the protein encoded by the nucleic acid comprises an about 95 percent identity or higher with a codon-optimized mutant Dnase1L3 of SEQ ID NO: 2-8. In another aspect, the mutant Dnase1L3 is post-translationally modified with polyethylene glycol. In another aspect, the mutant Dnase1L3 is post-translationally modified with a polyethylene glycol having a molecular mass from 5 kDa to 50 kDa.

In another embodiment, the present invention includes host cell transformed with an expression vector comprising a nucleic acid encoding an amino acid sequence of SEQ ID NO: 2-8 for a mutant Dnase1L3. In one aspect, the host cell comprises a bacterial or a yeast cell. In another aspect, the host cell comprises *E. coli, Pichia pastoris*, or a host strains that allows enhanced disulfide bond formation and enhanced expression of eukaryotic proteins that contain codons rarely used in *E. coli*.

In another embodiment, the present invention includes process for making a protein with DNase activity comprising the steps of: transforming a host cell with an isolated nucleic acid comprising a nucleotide sequence encoding a mutant Dnase1L3 protein with at least about an 95% identity with SEQ ID NO: 2-8 for a Dnase1L3; and culturing the host cell under conditions such that the mutant Dnase1L3 protein is produced by the host cell, wherein the mutant Dnase1L3 protein comprises at least one mutation for post-translational modification or attachment of a molecule to the mutant Dnase1L3 protein to increase the serum half-life of the mutant Dnase1L3 protein.

In another embodiment, the present invention includes mutant Dnase1L3 protein produced by a method comprising: culturing a bacterial or yeast host cell transformed with an expression vector comprising a DNA sequence comprising the nucleotide sequence encoding the mutant Dnase1L3 of SEQ ID NO:2-8, expressing the mutant Dnase1L3 in the cultured yeast host cell; and isolating the mutant Dnase1L3. In one aspect, the mutant Dnase1L3 is post-translationally modified with polyethylene glycol. In another aspect, the mutant Dnase1L3 is post-translationally modified with a polyethylene glycol having a molecular mass from 5 kDa to 50 kDa.

In another embodiment, the present invention includes process for making a mutant Dnase1L3 comprising the steps of: transforming a host cell with a nucleic acid molecule that encodes the mutant Dnase1L3 comprising an amino acid sequence of SEQ ID NO: 2-8; and culturing the host cell under conditions in which the mutant Dnase1L3 is produced by the host cell. In another aspect, the host cell comprises *E. coli* or *Pichia pastoris*. In another aspect, the host cell produces at least 1.0 mg/L mutant Dnase1L3 protein. In another aspect, the host cell produces at least 7.5 mg/L mutant Dnase1L3.

In another embodiment, the present invention includes mutant Dnase1L3 made by the process culturing a bacterial or yeast host cell transformed with an expression vector comprising a DNA sequence comprising the nucleotide sequence encoding the mutant Dnase1L3 of SEQ ID NO:2-8, expressing the mutant Dnase1L3 in the cultured yeast host cell; and isolating the mutant Dnase1L3. In one aspect, the mutant Dnase1L3 is post-translationally modified with polyethylene glycol. In another aspect, the mutant Dnase1L3 is post-translationally modified with a polyethylene glycol having a molecular mass from 5 kDa to 50 kDa.

BRIEF DESCRIPTION OF THE DRAWINGS

For a more complete understanding of the features and advantages of the present invention, reference is now made to the detailed description of the invention along with the accompanying figures and in which:

(FIG. 1A) Dnase1L3 was affinity purified with Nickel NTA agarose, then cleaved with Tobacco Etch Virus protease TEV protease. Cleaved Dnase1L3 was further purified by anion exchange and then by size exclusion chromatography. Fractions from the final size exclusion purification were resolved by SDS-PAGE and Coomassie stained. Fractions 7-9 show purified Dnase1L3 at the expected 36 kDa size. Molecular weight in kDa is shown. (FIG. 1B) The indicated amounts of purified Dnase1L3 were resolved by SDS-PAGE, transferred to nitrocellulose and probed with anti-Dnase1L3 primary antibody, anti-rabbit HRP secondary antibody and developed with enhanced chemiluminescence. (FIG. 1C) Recombinant, purified Dnase1L3 was incubated at increasing dilutions with 400 ng plasmid DNA for 30 min at 37° C. in 200 mM Tris pH 7.4, 50 mM MgCl2, 20 mM CaCl2 with or without 100 µM Dnase1L3 inhibitors fmoc-D-cyclohexylalanine (FCA) or Pontacyl Violet 6R (PV). Remaining plasmid DNA resolved on a 1% agarose gel. # indicates non-degraded DNA (i.e. supercoiled, nicked and linear DNA). The absence of DNA indicates degradation. (FIG. 1D) Purified Dnase1L3 was conjugated to PEG. Unconjugated Dnase1L3, PEGylated Dnase1L3 (PEG-D1L3), or free PEG were resolved by SDS-PAGE and visualized with Coomassie Blue. The 36 kDa band has increased in size to 41 kDa, indicating successful PEGylation. Molecular weight in kDa is shown. (FIG. 1E) PEGylated Dnase1L3 was incubated at increasing dilutions with 200 ng plasmid DNA for 30 min at 37° C. in 200 mM Tris pH 7.4, 50 mM MgCl2, and 20 mM CaCl2. Remaining plasmid DNA resolved on a 1% agarose gel. # indicates non-degraded DNA (i.e. supercoiled, nicked and linear DNA). The absence of DNA indicates degradation.

DETAILED DESCRIPTION OF THE INVENTION

Figure 1A:
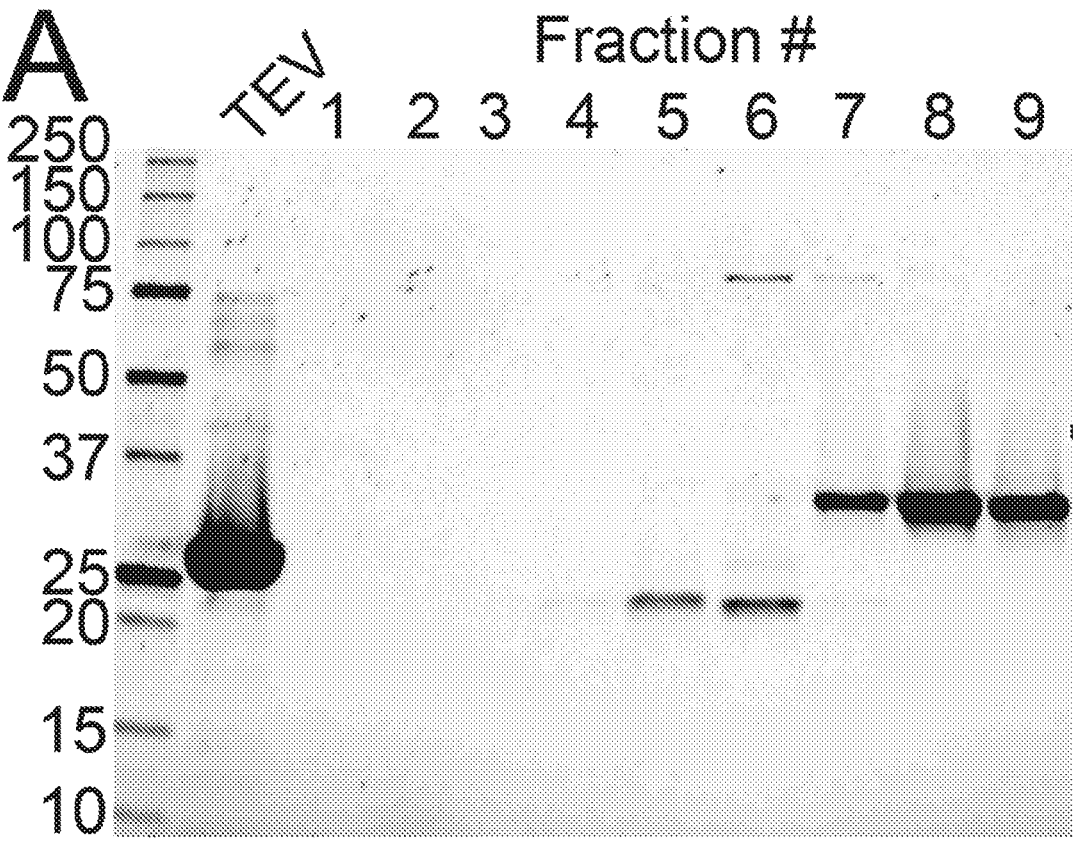
FIGS. 1A to 1E show the results from the modified Dnase1L3 of the present invention. PEGylated Dnase1L3 is a potent endonuclease.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present inventors have developed novel Dnase1L3 mutants for therapy. A problem with Dnase1L3 therapy is its short serum half-life. The present inventors have made key modifications to the protein Dnase1L3 that improves its serum half-life without compromising its activity. Dnase1L3 is a small (~33 kDa) protein, which is why it is assumed to have a short serum half-life. One general method to improve half-life is addition of polyethylene glycol (PEGylation), which increases the size of the protein and protects it from degradation. However, PEGylation has never been applied to Dnase1L3 due to the lack of residues for attachment. Adding PEG to Dnase1L3 requires modification of the protein to facilitate the chemical reaction, but the locations on the protein that can accept PEG without destroying protein function are unknown. Using homology modeling, the present inventors identified 3 novel sites on Dnase1L3 that can be mutated to accept PEG-ylation. These sites do not compromise nuclease activity, but are predicted to enhance the serum half-life of Dnase1L3. Enhancing serum half-life is a necessary prerequisite to developing Dnase1L3 as a therapy for any disease.

The present inventors targeted 3 different locations on the protein to mutate the residues to allow for PEGylation. Targeting these amino acids involves changing them from serine to cysteine any one of: S91C, S112C and/or S253C, because the PEGylation requires cysteine in those locations. PEGylation has not previously been applied to Dnase1L3. The present inventors used homology modeling to predict solvent-accessible amino acids that would not interfere with the enzyme activity. Targeted amino acids can also involve changing from serine to cysteine at S131C and/or S272C.

Target serines highlighted in bold and underlined, and numbered by full length Dnase1L3. *Homo sapiens*. Wild-type Dnase1L3 Primary Amino Acid sequence (amino acids 21-305 of the long isoform):

(SEQ ID NO: 1)
MRICSFNVRSFGESKQEDKNAMDVIVKVIKRCDIILVMEIKDSNNRICPIL

MEKLNRNSRRGITYNYVISSRLGRNTYKEQYAFLYKEKLVSVKRSYHYHD

YQDGDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQEDT

TVKKSTNCAYDRIVLRGQEIVSSVVPKSNSVFDFQKAYKLTEEEALDVSD

HFPVEFKLQSSRAFTNSKKSVTLRKKTKSKRS.

Mutant Dnase1L3 of the present invention, mutation at S91C (SEQ ID NO: 2)
MRICSFNVRSFGESKQEDKNAMDVIVKVIKRCDIILVMEIKDSNNRICPIL

MEKLNRNSRRGITYNYVISCRLGRNTYKEQYAFLYKEKLVSVKRSYHYHD

YQDGDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQEDT

TVKKSTNCAYDRIVLRGQEIVSSVVPKSNSVFDFQKAYKLTEEEALDVSD

HFPVEFKLQSSRAFTNSKKSVTLRKKTKSKRS.

Mutant Dnase1L3 of the present invention, mutation at S112C (SEQ ID NO: 3)
MRICSFNVRSFGESKQEDKNAMDVIVKVIKRCDIILVMEIKDSNNRICPIL

MEKLNRNSRRGITYNYVISSRLGRNTYKEQYAFLYKEKLVCVKRSYHYHD

YQDGDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQEDT

TVKKSTNCAYDRIVLRGQEIVSSVVPKSNSVFDFQKAYKLTEEEALDVSD

HFPVEFKLQSSRAFTNSKKSVTLRKKTKSKRS.

Mutant Dnase1L3 of the present invention, mutation at S253C (SEQ ID NO: 4)
MRICSFNVRSFGESKQEDKNAMDVIVKVIKRCDIILVMEIKDSNNRICPIL

MEKLNRNSRRGITYNYVISSRLGRNTYKEQYAFLYKEKLVSVKRSYHYHD

YQDGDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQEDT

TVKKSTNCAYDRIVLRGQEIVSSVVPKSNCVFDFQKAYKLTEEEALDVSD

HFPVEFKLQSSRAFTNSKKSVTLRKKTKSKRS.

Mutant Dnase1L3 of the present invention, mutation at S91C and S112C (SEQ ID NO: 5)
MRICSFNVRSFGESKQEDKNAMDVIVKVIKRCDIILVMEIKDSNNRICPIL

MEKLNRNSRRGITYNYVISCRLGRNTYKEQYAFLYKEKLVCVKRSYHYHD

YQDGDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQEDT

TVKKSTNCAYDRIVLRGQEIVSSVVPKSNSVFDFQKAYKLTEEEALDVSD

HFPVEFKLQSSRAFTNSKKSVTLRKKTKSKRS.

Mutant Dnase1L3 of the present invention, mutation at S91C and S253C (SEQ ID NO: 6)
MRICSFNVRSFGESKQEDKNAMDVIVKVIKRCDIILVMEIKDSNNRICPIL

MEKLNRNSRRGITYNYVISCRLGRNTYKEQYAFLYKEKLVSVKRSYHYHD

YQDGDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQEDT

TVKKSTNCAYDRIVLRGQEIVSSVVPKSNCVFDFQKAYKLTEEEALDVSD

HFPVEFKLQSSRAFTNSKKSVTLRKKTKSKRS.

Mutant Dnase1L3 of the present invention, mutation at S112C and S253C (SEQ ID NO: 7)
MRICSFNVRSFGESKQEDKNAMDVIVKVIKRCDIILVMEIKDSNNRICPIL

MEKLNRNSRRGITYNYVISSRLGRNTYKEQYAFLYKEKLVCVKRSYHYHD

YQDGDADVFSREPFVVWFQSPHTAVKDFVIIPLHTTPETSVKEIDELVEVY

-continued

TDVKHRWKAENFIFMGDFNAGCSYVPKKAWKNIRLRTDPRFVWLIGDQEDT

TVKKSTNCAYDRIVLRGQEIVSSVVPKSNCVFDFQKAYKLTEEEALDVSD

HFPVEFKLQSSRAFTNSKKSVTLRKKTKSKRS.

Mutant Dnase1L3 of the present invention, mutation at S91C, S112C, and S253C (SEQ ID NO: 8)

MRICSFNVRSFGESKQEDKNAMDVIVKVIKRCDIILVMEIKDSNNRICPIL

MEKLNRNSRRGITYNYVISCRLGRNTYKEQYAFLYKEKLVCVKRSYHYHD

YQDGDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQEDT

TVKKSTNCAYDRIVLRGQEIVSSVVPKSNCVFDFQKAYKLTEEEALDVSD

HFPVEFKLQSSRAFTNSKKSVTLRKKTKSKRS.

Additional variable peptide sequences N-terminal to Dnase1L3 due to protease cleavage may also be present.

Example Primers used to mutate serines to cysteines in Dnase1L3:

S91C (SEQ ID NO: 9)
5'- CGT ACA ACT ATG TGA TTA GCT GTC GGC TTG GAA GAA

ACA C -3'

(SEQ ID NO: 10)
5'- GTG TTT CTT CCA AGC CGA CAG CTA ATC ACA TAG TTG

TAC G -3'

S112C (SEQ ID NO: 11)
5'- CTA CAA GGA AAA GCT GGT GTG TGT GAA GAG GAG TTA

TC -3'

(SEQ ID NO: 12)
5'- GAT AAC TCC TCT TCA CAC ACA CCA GCT TTT CCT TGT

AG -3'

S253C (SEQ ID NO: 13)
5'- GTT CCC AAG TCA AAC TGT GTT TTT GAC TTC CAG AAA

GC -3'

(SEQ ID NO: 14)
5'- GCT TTC TGG AAG TCA AAA ACA CAG TTT GAC TTG GGA

AC -3'

Method. Mutations were introduced into Dnase1L3 by Quickchange mutagenesis: 10-30 ng of Dnase1L3 was mixed with 200 nM of each primer, 300 μM dNTP, and 1 U Verity Pfu in 1× Verity PCR buffer (catalog #31-5020, Tonbo Biosciences, San Diego Calif.). PCR was run on a BioRad T100 thermal cycler using the following program: (Lid 104 C), 1. 95° C. 1 min, 2. 95° C. 30 sec, 3. 55° C. 1 min, 4. 68° C. 12 min, 5. Go to 2, repeat 18 times, 6. 68° C. 15 min, 7. 4° C. forever.

At step 7, PCR product was removed from the PCR machine, optionally cleaned using the Wizard SV Gel and PCR Clean-up System (catalog #A9282 Promega, Madison, WI) according to manufacturer's instructions.

The PCR product was DpnI digested with the addition of Cutsmart buffer and 20 U DpnI (catalog #R0176 New England Biolabs, Ipswich, MA), incubation at 37° C. for 1 h.

The Dpn-digest was transformed into subcloning efficiency DH5a bacterial cells (catalog #18265017 Invitrogen, Waltham, MA). DNA and bacteria were incubated on ice for 20 min, heat shocked at 37° C. for 20 seconds, and incubated on ice for 2 min. To the bacteria, 0.95 mL LB was added. Bacteria were placed on a shaker at 225×rpm for 1 h at 37° C., then centrifuged 10,000×g for 5 min at room temp. 0.9 mL LB was removed. Bacteria were resuspended in the remaining 100 uL and plated overnight at 37° C. on LB agar with Kanamycin. Colonies were inoculated into 2 mL LB broth, shaken at 225×rpm 37° C. overnight. DNA was extracted from overnight cultures using miniprep kit (catalog #: 2160250, Epoch Life science, Sugar Land, TX) per manufacturer's instructions and sequenced by Sanger sequencing at Genewiz (New Brunswick, NJ). Once mutants were confirmed by sequencing, they were transformed into Rosetta-gami or BL21 cells.

After purification, Dnase1L3 was conjugated to PEG using the following method:

1) a) If Protein solution was eluted from size exclusion column in a buffer containing dithiothreitol (DTT):

Concentrate protein to less than or equal to 2.5 ml

Using PD-10 G25 desalting column

Degas $1^{st}$ buffer (300 mM NaCl, 1 mM $CaCl_2$, 20 mM HEPES pH 7.4) for 10 min in vacuum chamber set to 635 mm Hg Equilibrate column with 25 ml of $1^{st}$ buffer Discard flow through Add sample (purified protein at a volume of 2.5 ml-if needed add more of 1st buffer to make up volume to 2.5 ml)

Save flow through

Elute with 3.5 ml of degassed Elution buffer (300 mM, 1 mM $CaCl_2$, 20 mM HEPES pH 7.4, 1 mM Tris(2-carboxyethyl)phosphine (TCEP))

Collect elution in fractions of 0.3 ml

Measure $A_{280}$ using nanodrop and save fractions corresponding to peak b) If Protein is not in a solution containing DTT:

Add Tris(2-carboxyethyl)phosphine (TCEP) to Dnase1L3 protein solution to final concentration: 300 mM NaCl, 1 mM $CaCl_2$, 20 mM HEPES pH 7.4, 1 mM TCEP Degas protein solution for 10 min in vacuum chamber set to 635 mmHg 2) Ensure protein is concentrated to at least 0.05 mg/mL. Incubate TCEP with the protein for at least 10 min at 4° C. before adding maleimide.

3) Calculate protein concentration in μM for the saved fractions using the formula: [Dnase1L3](μM)=(μg/ml)/(MW in KDa). The concentration in μg/ml is determined by dividing the absorption at 280 nm ($A_{280}$) by the extinction coefficient. The extinction coefficient of Dnase1L3 is 1.195. MW in KDa is 36. Therefore, the molarity calculation is [Dnase1L3](μM)=$A_{280}$/43.02

4) Determine the volume of PEG-maleimide to add, using the following formula:

$$\text{Volume of PEG-maleimide} = [\text{PEG-maleimide}]_{final}*$$
$$(\text{Volume of Dnase1L3})/[\text{PEG-maleimide}]_{stock}$$

9

10

Prepare the PEG-maleimide stock solution at 1 mM to 10 mM. [PEG-maleimide]$_{final}$ is determined as follows:

$$[PEG\text{-}maleimide]_{final}{=}6*(\#mutated\ Cys)*$$
$$[Dnase1L3].$$

For PEG 5K maleimide use MW=5000 g/mol

5) Incubate PEG-maleimide and Dnase1L3 overnight at 4° C. Assess PEGylation by SDS-PAGE.

Figure 1B:
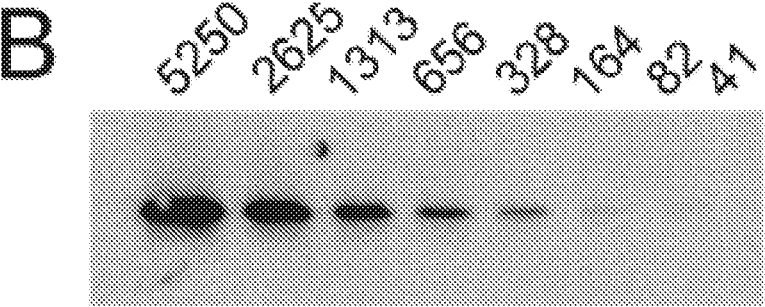
Figure 1C:
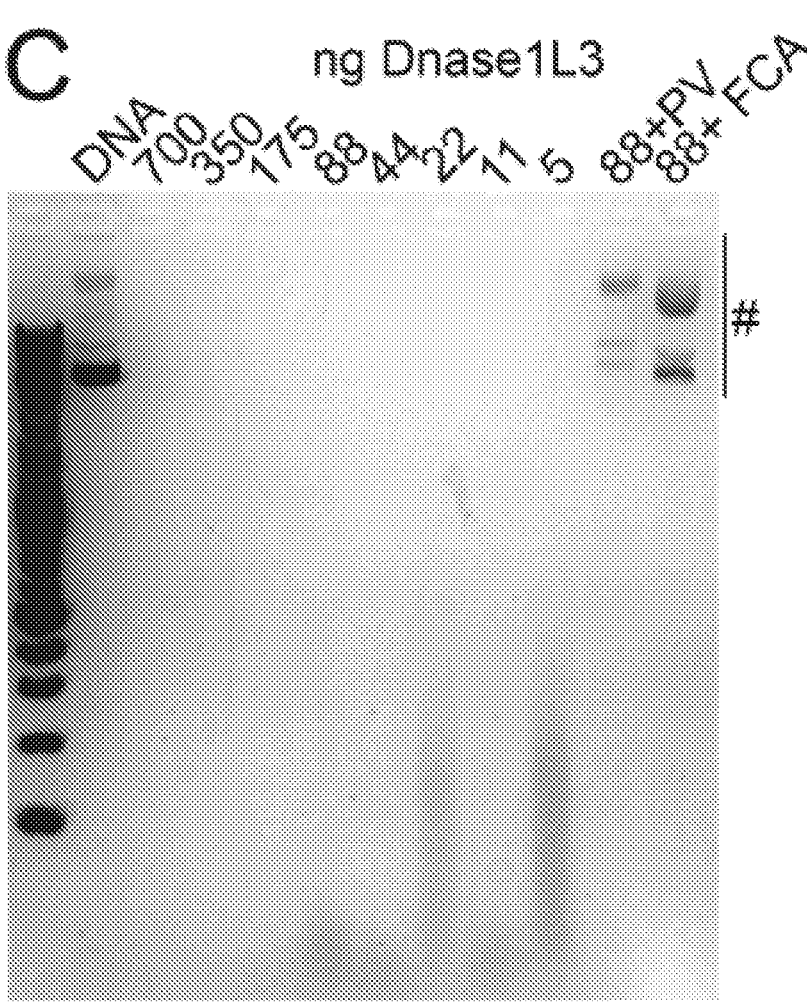
Figure 1D:
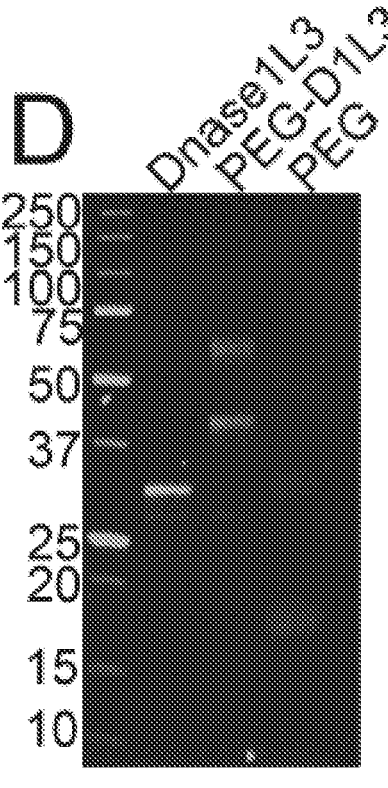
Figure 1E:

FIGS. 1A to 1E show the results from the modified Dnase1L3 of the present invention. PEGylated Dnase1L3 is a potent endonuclease. FIG. 1A shows the results when Dnase1L3 was affinity purified with Nickel NTA agarose, then cleaved with Tobacco Etch Virus protease TEV protease. Cleaved Dnase1L3 was further purified by anion exchange and then by size exclusion chromatography. Fractions from the final size exclusion purification were resolved by SDS-PAGE and Coomassie stained. Fractions 7-9 show purified Dnase1L3 at the expected 36 kDa size. Molecular weight in kDa is shown. FIG. 1B shows the results when the indicated amounts of purified Dnase1L3 were resolved by SDS-PAGE, transferred to nitrocellulose and probed with anti-Dnase1L3 primary antibody, anti-rabbit HRP secondary antibody and developed with enhanced chemiluminescence. FIG. 1C shows the results when recombinant, purified Dnase1L3 was incubated at increasing dilutions with 400 ng plasmid DNA for 30 min at 37° C. in 200 mM Tris pH 7.4, 50 mM MgCl$_2$, 20 mM CaCl$_2$ with or without 100 μM Dnase1L3 inhibitors fmoc-D-cyclohexylalanine (FCA) or Pontacyl Violet 6R (PV). Remaining plasmid DNA was resolved on a 1% agarose gel. # indicates non-degraded DNA (i.e. supercoiled, nicked and linear DNA). The absence of DNA indicates degradation. FIG. 1D shows the results when purified Dnase1L3 was conjugated to PEG. Unconjugated Dnase1L3, PEGylated Dnase1L3 (PEG-D1L3), or free PEG were resolved by SDS-PAGE and visualized with Coomassie Blue. The 36 kDa band has increased in size to 41 kDa, indicating successful PEGylation. Molecular weight in kDa is shown. FIG. 1E shows the results when PEGylated Dnase1L3 was incubated at increasing dilutions with 200 ng plasmid DNA for 30 min at 37° C. in 200 mM Tris pH 7.4, 50 mM MgCl2, and 20 mM CaCl2. Remaining plasmid DNA resolved on a 1% agarose gel. # indicates non-degraded DNA (i.e. supercoiled, nicked and linear DNA). The absence of DNA indicates degradation.

Purification Protocol

A. Induction

1. Transform competent Rosetta-gami cells with Dnase1L3 in p202:

a. Thaw competent Rosetta-gami cells from −80° C. on ice.

b. Mix 1 μl of plasmid DNA (20-40 pg) with 50 μl of bacterial cells in a 1.5 ml tube.

c. Incubate the mixture on ice for 20 minutes.

d. Heat-shock the mixture at 42° C. in water bath for 45 sec.

e. Put the tube back on ice for 2 min.

f. Add 250 μl SOC or LB broth, without antibiotic, to the 1.5 ml tube and shake at 250 rpm at 37° C. for 1 hour.

g. Place LB agar plate containing 50 μg/mL Kanamycin in incubator alongside mixture to warm up the plate from 4° C.

h. Spread contents of the 1.5 ml tube on the agar plate and incubate at 37° C. overnight.

2. Sample multiple colonies and add them to 150 ml LB (with 150 μl 50 mg/ml Kanamycin) in an autoclaved 250 ml culture flask with baffles.

3. Shake flask at 250 rpm at 37° C. for 20 hours to prepare the overnight culture.

4. Transfer 20 ml overnight culture to each of 6 autoclaved 1-liter culture flasks containing 1 L of terrific broth (TB) supplemented with 0.1 M potassium phosphate buffer. Potassium phosphate buffer can be formulated directly in TB or add 100 ml 1 M potassium phosphate buffer per liter TB.

5. Add 1 ml 50 mg/ml Kanamycin to each 1-liter culture flasks, then shake at 250 rpm at 37° C. until the OD600 reaches 1.5 to 1.8 (typically 7 hours).

6. When the OD600 reaches 1.5-1.8, turn temperature down to 18° C., 1 hour later induce each culture with 400 μl of 1 M Isopropyl β-D-1-thiogalactopyranoside (IPTG). Shake at 250 rpm in 18° C. for 10 more hours.

7. Transfer culture flasks to 1 L centrifuge tubes and centrifuge at 6200×g for 15 min at 4° C. to pellet cells.

8. Save pellet, discard supernatant.

9. Transfer pellets to 50 ml screw top tubes, with 2 pellets to a tube, freeze all tubes at −80° C.

B. Lysis

1. Resuspend frozen pelleted cells from 2 1-liter cultures in 200 ml PMSF Lysis buffer. Use freshly prepared PMSF.

a. PMSF Lysis buffer: 300 mM NaCl, 5 mM CaCl$_2$, 20 mM HEPES, 1 mM PMSF pH 7.4.

2. Mechanically lyse resuspended cells in a Microfluidizer Processor M-110EH.

3. Spin down at 45,900×g for 45 min at 4° C. in centrifuge.

4. Save supernatant for EITHER C. First Purification Step Using Nickel Column OR D. First Purification Step Using Amylose Resin.

C. First Purification Step Using Nickel Column

1. Clean Nickel Column (filled with 30 ml Ni-NTA agarose).

b. Fill Column with 100 ml of 0.1 M Ethylenediaminetetraacetic acid (EDTA) pH 8.

c. Rinse Column with 2 column volumes of dH$_2$O.

2. Prime NTA-agarose with Nickel d. Fill Column with 50 ml of 100 mM NiSO$_4$.

e. Rinse Column with 2 column volumes of dH$_2$O.

3. Equilibrate NTA-agarose Ni Column f. Fill Column w/50 ml of Lysis Buffer.

4. Bind Lysate to NTA-agarose Beads g. Transfer Lysate and beads to large enough beaker.

h. Allow to bind in 4° C. refrigerator for 2 hours.

5. Wash Lysate i. Pour lysate and beads back into column, gently.

j. Allow lysate to go through filter, collect, save 20 μl fraction for SDS page as "ni col. flowthrough".

k. Wash column with 100 ml lysis buffer, collect, save 20 μl fraction for SDS page as "ni col. wash".

l. Wash column with 100 ml 30 mM imidazole buffer, collect, save 20 μl fraction for SDS page as "ni col 30 mM imi".

i. 30 mM imidazole buffer: 5 mM Maltose, 1 mM CaCl$_2$, 150 mM NaCl, 20. mM HEPES, 30 mM imidazole; pH 7.4.

6. Elute column m. Elute column in 50 ml 250 mM imidazole buffer, collect, save 20 μl fraction for SDS page as "ni col 250 mM imi uncut".

i. 250 mM imidazole buffer: 5 mM Maltose, 1 mM CaCl$_2$, 150 mM NaCl, 20 mM HEPES, 250 mM imidazole; pH 7.4.

7. Add 1 ml 5 mg/ml Tobacco Etch Virus (TEV) protease to eluate and incubate overnight at 4° C. Save 20 μl fraction for SDS page as "ni col 250 mM imi cut with TEV".

8. Resolve samples reserved above by SDS-PAGE (Mini-proteanTGX Stain-Free Any kD (unique formulation)). Verify presence of Dnase1L3 in eluate (~80 kDa fusion protein, ~33 kDa cut protein) and proceed to E. S Sepharose column.

D. First Purification Step Using Amylose Resin.

1. Pour prepared amylose resin (see H) into 100 ml volume column with frit.

2. Wash resin with three column volumes of dH$_2$O and then one column volume of Lysis buffer.

3. Cap bottom of column, pour lysate over resin, seal, and leave at 4° C. overnight to bind.

4. Wash and elute the column as follows:
   a. Collect column flowthrough, save 20 μl fraction for SDS page as flowthrough 1.
   b. Wash column with 100 ml Lysis buffer, save 20 μl fraction for SDS page as wash 1.
   c. Elute column with 75 ml maltose buffer, save 20 μl fraction for SDS page as elution 1.
      i. Maltose buffer: 300 mM NaCl, 1 mM CaCl$_2$, 40 mM maltose, 20 mM HEPES pH 7.4.

5. Run the flowthrough again with 5 ml of fresh amylose resin by repeating step D.1-3.

6. Repeat elution step D.4 again, but save fractions as (respectively): flowthrough 2, wash 2, and elution 2.

7. Run the flowthrough from step D.6 through used amylose resin from step D.5.

8. Repeat step D.4, saving fractions as (respectively): flowthrough 3, wash 3, and elution 3.

9. Add 1 ml 5 mg/ml Tobacco Etch Virus(TEV) protease to each eluate and incubate overnight at 4° C. In the morning collect 20 μl fraction for SDS page from each elution with TEV protease added as (respectively): elution 1 with TEV, elution 2 with TEV, and elution 3 with TEV.

10. Resolve samples reserved above by SDS-PAGE (Mini-proteanTGX Stain-Free Any kD (unique formulation)). Verify presence of Dnase1L3 in each eluate by mass. Combine elutions containing Dnase1L3 and proceed to E. S Sepharose column.

E. S Sepharose Column

1. Combine column eluate containing Dnase1L3 and dilute 2:1, eluate:buffer using A buffer.
   a. A buffer: 50 mM NaCl, 1 mM CaCl2, 20 mM HEPES, pH 7.4.

2. Prepare FPLC by turning on UV absorbance detector/emitter and washing sulphopropyl (SP) sepharose column with A buffer (roughly 60 ml).

3. Load diluted Nickel column eluate, collect waste line for SDS page.

4. Run A buffer for 50 ml to bring down [NaCl] in the lines.

5. Run gradient of increasing salt concentration using B buffer for 18 min, and collect 3 ml fractions.
   a. B buffer: 1 M NaCl, 1 mM CaCl2, 20 mM HEPES, pH 7.4.

6. Resolve fractions by SDS-PAGE to determine which UV absorbance peak corresponds to Dnase1L3.

7. Pool the fractions that contain Dnase1L3.

F. Size Exclusion Chromatography

1. Prepare the FPLC using the size exclusion chromatography column (Superdex 75) by ensuring the UV absorbance detector is on and washing the column with 200 ml of SEC buffer.
   a. SEC buffer: 150 mM NaCl, 1 mM CaCl2, 20 mM HEPES, pH 7.4.

2. Concentrate to <1 ml the combined fractions from the S Column that contained Dnase1L3 as shown by the last gel.
   a. Concentrate using centrifugal filter, and centrifuging at 5000×g at 4° C. in 15 ml. increments, mixing in between centrifugation, until volume between 0.8 and 1 ml.

3. Inject the concentrated Dnase1L3 into the FPLC loop.

4. Load onto column with SEC buffer, collecting 3 ml fractions 50 ml later.

5. Run fractions on SDS page gel to determine the UV absorbance peak that corresponds to Dnase1L3.

6. Save fractions that correspond to Dnase1L3 on peak UV absorbance and SDS-PAGE.

G. Buffers and Solutions

Potassium Phosphate Buffer: 23.1 g KH$_2$PO$_4$ and 125.4 g K$_2$HPO$_4$ per 1 L.

Terrific Broth: Tryptone 12 g, Yeast Extract 24 g, 50% b/v glycerol 8 ml, 892 ml water; per 1 L LB Broth: Tryptone 10 g, Yeast Extract 5 g, NaCl 10 g.

LB Agar Plates: Tryptone 10 g, Yeast Extract 5 g, NaCl 10 g, Agar 15 g; per 1 L

PMSF Lysis buffer: 300 mM NaCl, 5 mM CaCl$_2$, 1 mM PMSF, 20 mM HEPES, pH 7.4 Difco LB Broth, Miller: 12.5 g of LB Media per 500 ml.

Lysis buffer: 5 mM Maltose, 150 mM NaCl, 1 mM CaCl$_2$, 20 mM HEPES, pH 7.4.

Maltose buffer: 300 mM NaCl, 1 mM CaCl$_2$, 40 mM maltose, 20 mM HEPES pH 7.4.

A buffer: 50 mM NaCl, 1 mM CaCl$_2$, 20 mM HEPES, pH 7.4.

B buffer: 1 M NaCl, 1 mM CaCl$_2$, 20 mM HEPES, pH 7.4.

SEC buffer: 300 mM NaCl, 1 mM CaCl$_2$, 20 mM HEPES, pH 7.4.

30 mM imidazole buffer: 5 mM Maltose, 1 mM CaCl$_2$, 150 mM NaCl, 20 mM HEPES, 30 mM imidazole; pH 7.4.

250 mM imidazole buffer: 5 mM Maltose, 1 mM CaCl$_2$, 150 mM NaCl, 20 mM HEPES, 250 mM imidazole; pH 7.4.

Amylose Prep Solution: 0.5 M NaCl, 50 mM glycine-HCL; pH 2.0.

H. Amylose Resin Preparation

1. Evenly suspend 10 g amylose (Sigma, grade III from potato) in 40 ml water. Warm suspension to 50° C. in water bath for 10 min.

2. Add 60 ml 5 M NaOH while stirring rapidly. Then add 30 ml epichlorohydrin while continuing to stir rapidly. This suspension should solidify into a gel within 10 min, when the suspension begins to solidify stop stirring. Allow the gel to cool to room temperature and incubate at room temperature for 45 min.

3. Wash gel with 200 ml of dH$_2$O and transfer to a blender. Fragment the gel by blending 3-4 times in 7 second intervals at low speed using 200 watt hand blender, in a suspension of water. Wash again in dH$_2$O.

4. Transfer broken gel to a graduated cylinder and resuspend in 100 ml of Amylose prep solution. Between each wash allow the gel to settle, to separate fine crosslinked amylose particles left in the supernatant.

Once settled decant the supernatant by pouring off supernatant, and repeat resuspension then decantation of amylose particles 2 more times for a total of 3 washes.

5. Amylose prep solution: 0.5 M NaCl, 50 mM glycine-HCl, pH 2.0.
6. Resuspend and decant two more times as in step H.4 replacing amylose prep solution with dH$_2$O.
7. Can be stored in 20% ethanol.

Figure 2:
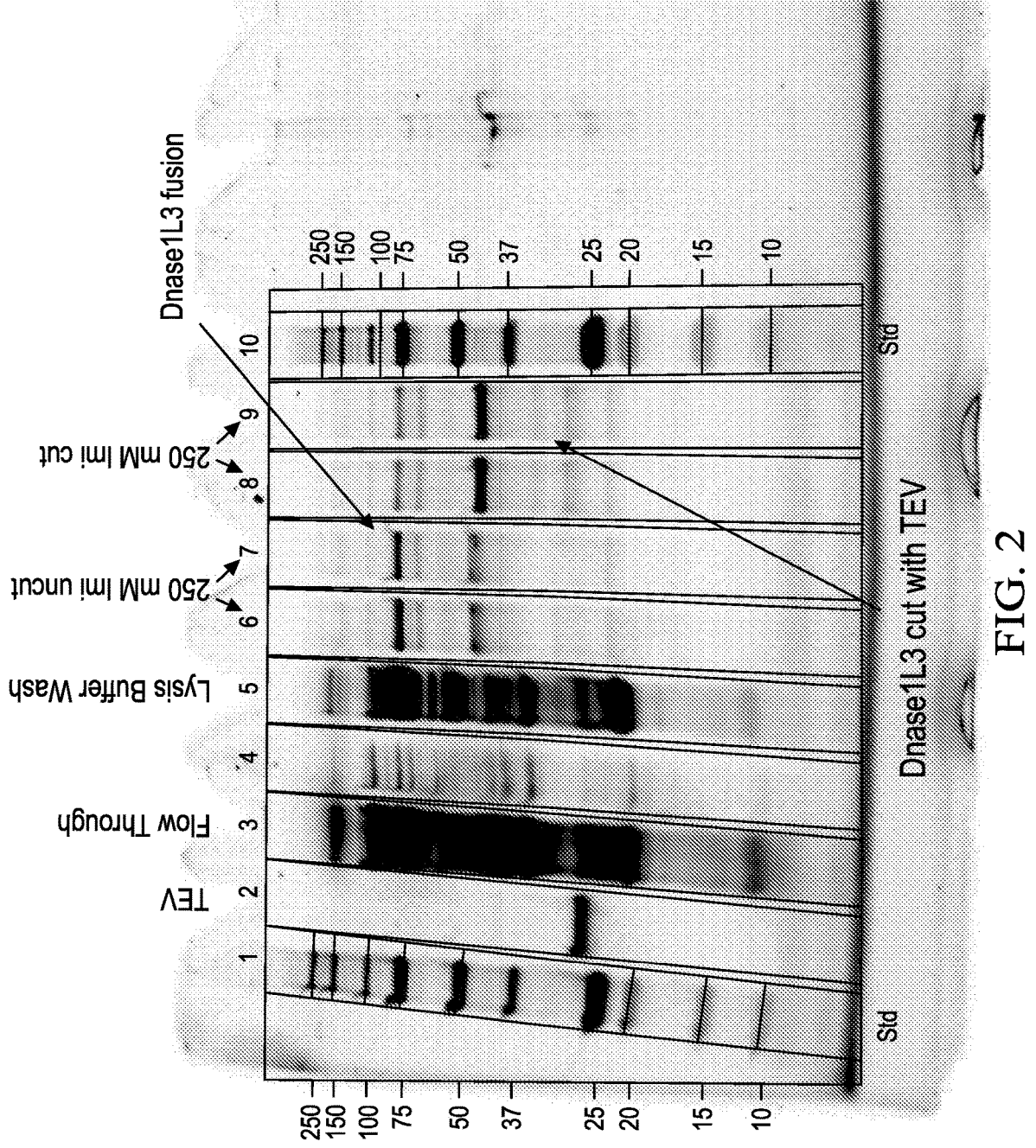
FIG. 2 shows the initial Purification of Dnase1L3. Samples collected during Nickel-NTA purification and TEV cleavage of MBP-Dnase1L3 were resolved by SDS-PAGE. Flowthrough is the sample described in step C.5j, Lysis Buffer in step B. 1a, 250 mM Imi uncut in step C.6m, 250 mM Imi cut in step C.7. MBP-Dnase1L3 is ~77 kDa in size, cut Dnase1L3 is ~33 kDa, free MBP is ~44 kDa and TEV ~30 kDa.

FIG. 2 shows the initial Purification of Dnase1L3. Samples collected during Nickel-NTA purification and TEV cleavage of MBP-Dnase1L3 were resolved by SDS-PAGE. Flowthrough is the sample described in step C.5j, Lysis Buffer in step B1a, 250 mM Imi uncut in step C.6m, 250 mM Imi cut in step C.7. MBP-Dnase1L3 is ~77 kDa in size, cut Dnase1L3 is ~33 kDa, free MBP is ~44 kDa and TEV ~30 kDa.

Figure 3:
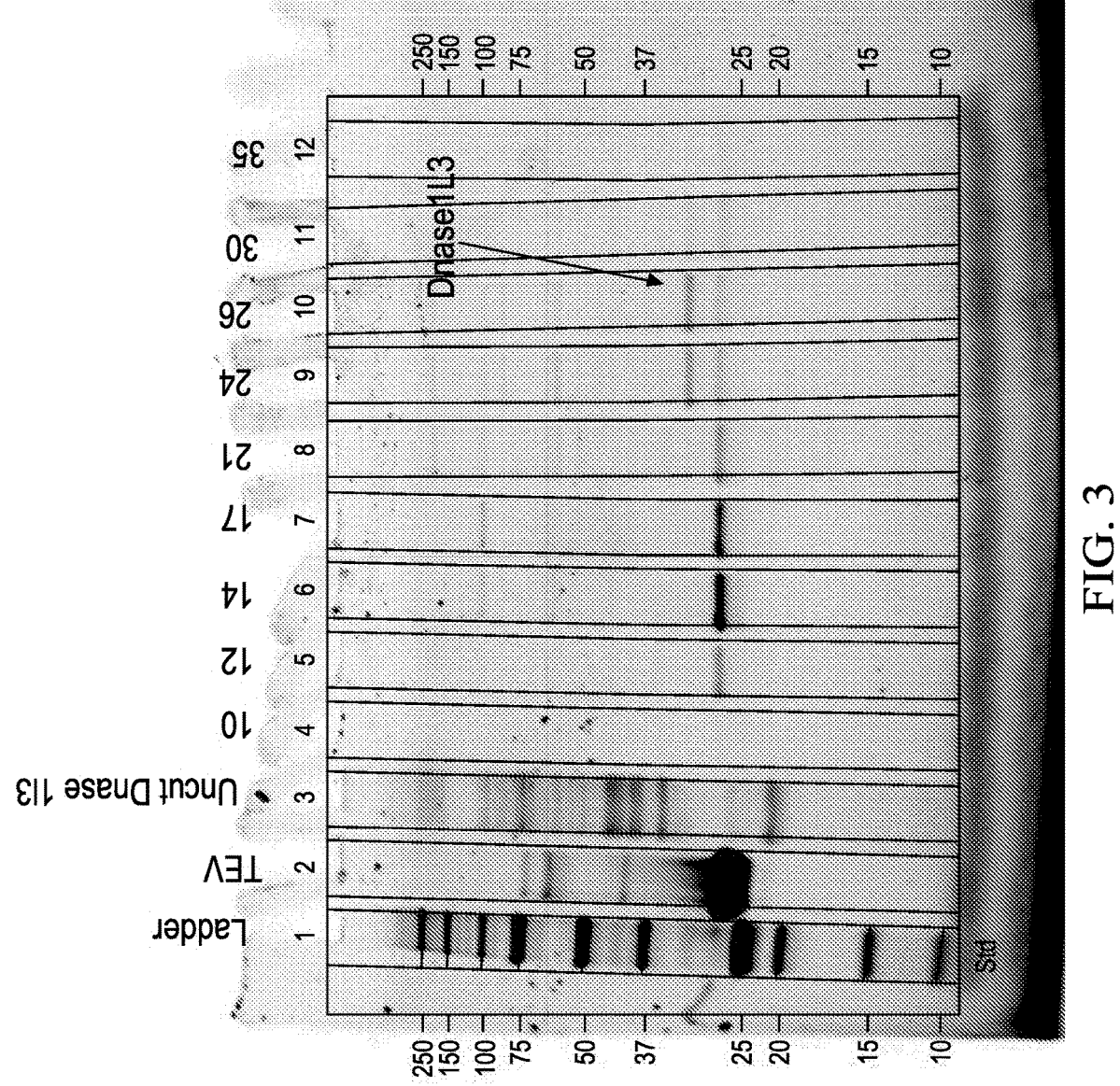
FIG. 3 shows the purification of Dnase1L3 by Ion Exchange Chromatography. Cut Dnase1L3 was concentrated and loaded onto an FPLC equipped with an S column, and eluted with an increasing salt gradient. Purified TEV, uncut Dnase1L3, Step C.6m or the indicated fractions (in red) from the S column were resolved by SDS-PAGE. Dnase1L3 was present in fractions 24 to 30.

FIG. 3 shows the purification of Dnase1L3 by Ion Exchange Chromatography. Cut Dnase1L3 was concentrated and loaded onto an FPLC equipped with an S column, and eluted with an increasing salt gradient. Purified TEV, uncut Dnase1L3 from step C.6m or the indicated fractions (in red) from the S column were resolved by SDS-PAGE. Dnase1L3 was present in fractions 24 to 30.

Figure 4:
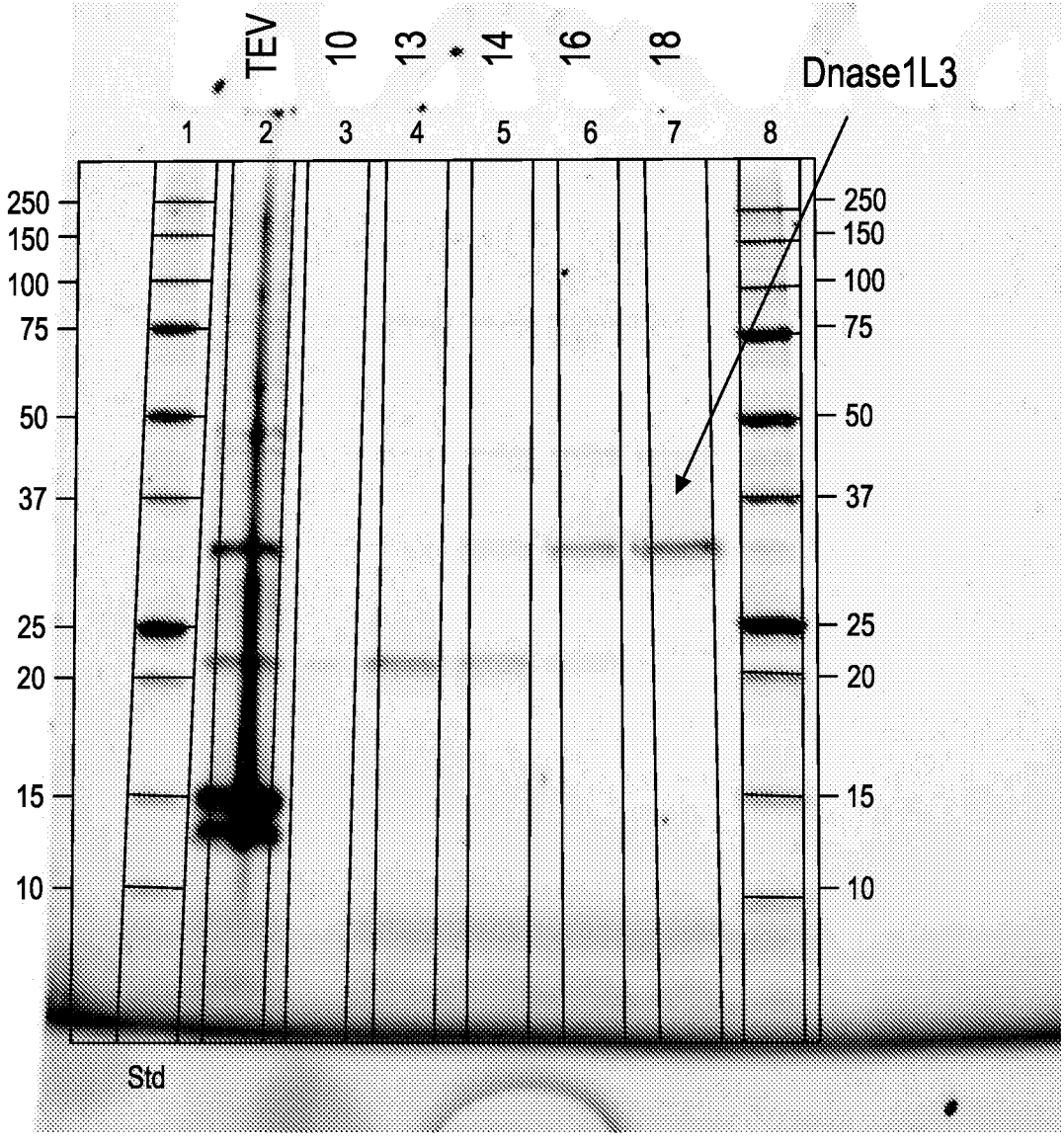
FIG. 4 shows the final purification of Dnase1L3 yields 96%+ purity. Dnase1L3 from the previous purification was concentrated, loaded onto and FPLC equipped with a Size exclusion column attached, and fractions (indicated in red) collected. Purified TEV or the indicated fractions were resolved by SDS-PAGE. Dnase1L3 eluted in fractions 16-18 in contrast to impurities that eluted in fractions 13-14.

FIG. 4 shows the final purification of Dnase1L3, which yields 95%+ purity. Dnase1L3 from the previous purification was concentrated, loaded onto and FPLC equipped with a Size exclusion column attached, and fractions (indicated in red) collected. Purified TEV or the indicated fractions were resolved by SDS-PAGE. Dnase1L3 eluted in fractions 16-18 in contrast to impurities that eluted in fractions 13-14.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A mutant Dnase1L3 nucleotide sequence having at least about a 95% identity with a nucleic acid sequence encoding a mutant Dnase1L3 protein having SEQ ID NO: 2-8, wherein the mutant Dnase1L3 protein comprises at least one mutation for post-translational modification or attachment of a molecule to the mutant Dnase1L3 to increase a serum half-life of the mutant Dnase1L3, wherein the mutation to Dnase1L3 protein is selected from at least one of:

an S112C mutation, an S131C mutation, or an S279C mutation; or at least two mutations selected from S91C, S112C, S131C, and S279C.

2. The mutant Dnase1L3 nucleotide sequence of claim 1, further comprising a nucleic acid sequence optimized for microbial expression.

3. The mutant Dnase1L3 nucleotide sequence of claim 1, wherein: the mutant Dnase1L3 protein further comprises at least one of S91C, an S131C or an S253C.

4. The mutant Dnase1L3 nucleotide sequence of claim 1, wherein the nucleotide sequence further comprises a nucleic acid segment encoding a leader sequence.

5. The mutant Dnase1L3 nucleotide sequence of claim 1, wherein said nucleotide sequence encodes a Dnase1L3 protein, wherein said protein is post-translationally modified with polyethylene glycol; or is post-translationally modified with a polyethylene glycol having a molecular mass from 5 kDa to 50 kDa.

6. A mutant Dnase1L3 protein produced by a method comprising:

culturing a host cell transformed with an expression vector comprising a DNA sequence comprising a nucleotide sequence encoding the mutant Dnase1L3 protein having at least 95% identity with SEQ IDS NO: 2-8; expressing the mutant Dnase1L3 protein in the host cell; and isolating the mutant Dnase1L3 protein, wherein the mutation to Dnase1L3 protein is selected from at least one of:

an S112C mutation, an S131C mutation, or an S279C mutation; or at least two mutations selected from S91C, S112C, S131C, and S279C.

7. The mutant Dnase1L3 protein of claim 6, wherein the mutant Dnase1L3 protein is post-translationally modified with polyethylene glycol; or the mutant Dnase1L3 protein is post-translationally modified with a polyethylene glycol having a molecular mass from 5 kDa to 50 kDa.

8. The mutant Dnase1L3 protein of claim 6, wherein the mutant Dnase1L3 protein further comprises at least one of: an S91C, an S131C, or an S253C mutation.

9. The mutant Dnase1L3 protein of claim 6, wherein the host cell encoding said protein comprises *E. coli* or *Pichia pastoris*.

10. The mutant Dnase1L3 protein of claim 6, wherein the host cell encoding said protein produces at least 0.25 or 7.5 mg/L mutant Dnase1L3 protein.

11. A mutant Dnase1L3 protein comprising at least about a 95% identity with SEQ ID NO: 2-8, wherein the Dnase1L3 protein comprises at least one mutation selected from:

An S112C mutation, an S131C mutation, or an S279C mutation; or

At least two mutations selected from S91C, S112C, S131C and S279C.

12. The mutant Dnase1L3 protein of claim 11, wherein the mutant Dnase1L3 protein is post-translationally modified with polyethylene glycol; or the mutant Dnase1L3 protein is post-translationally modified with a polyethylene glycol having a molecular mass from 5 kDa to 50 kDa.

13. The mutant Dnase1L3 protein of claim 11, wherein the mutant Dnase1L3 protein further comprises at least one of: an S91C, an S131C, or an S253C mutation.

* * * * *

SEQUENCE LISTING

<160> NUMBER OF SEQ ID NOS: 14

<210> SEQ ID NO 1
<211> LENGTH: 285
<212> TYPE: PRT
<213> ORGANISM: Artificial Sequence
<220> FEATURE:
<223> OTHER INFORMATION: Synthetic peptide

<400> SEQUENCE: 1

Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
        35                  40                  45

Pro Ile Leu Met Glu Lys Leu Asn Arg Asn Ser Arg Arg Gly Ile Thr
    50                  55                  60

Tyr Asn Tyr Val Ile Ser Ser Arg Leu Gly Arg Asn Thr Tyr Lys Glu
65                  70                  75                  80

Gln Tyr Ala Phe Leu Tyr Lys Glu Lys Leu Val Ser Val Lys Arg Ser
            85                  90                  95

Tyr His Tyr His Asp Tyr Gln Asp Gly Asp Ala Asp Val Phe Ser Arg
            100                 105                 110

Glu Pro Phe Val Val Trp Phe Gln Ser Pro His Thr Ala Val Lys Asp
        115                 120                 125

Phe Val Ile Ile Pro Leu His Thr Thr Pro Glu Thr Ser Val Lys Glu
    130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
            165                 170                 175

Val Pro Lys Lys Ala Trp Lys Asn Ile Arg Leu Arg Thr Asp Pro Arg
            180                 185                 190

Phe Val Trp Leu Ile Gly Asp Gln Glu Asp Thr Thr Val Lys Lys Ser
        195                 200                 205

Thr Asn Cys Ala Tyr Asp Arg Ile Val Leu Arg Gly Gln Glu Ile Val
    210                 215                 220

Ser Ser Val Val Pro Lys Ser Asn Ser Val Phe Asp Phe Gln Lys Ala
225                 230                 235                 240

Tyr Lys Leu Thr Glu Glu Glu Ala Leu Asp Val Ser Asp His Phe Pro
            245                 250                 255

Val Glu Phe Lys Leu Gln Ser Ser Arg Ala Phe Thr Asn Ser Lys Lys
            260                 265                 270

Ser Val Thr Leu Arg Lys Lys Thr Lys Ser Lys Arg Ser
        275                 280                 285

<210> SEQ ID NO 2
<211> LENGTH: 285
<212> TYPE: PRT
<213> ORGANISM: Artificial Sequence
<220> FEATURE:
<223> OTHER INFORMATION: Synthetic peptide

<400> SEQUENCE: 2

Met Arg Ile Cys Ser Phe Asn Val Arg Ser Phe Gly Glu Ser Lys Gln
1               5                   10                  15

-continued

```
Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
            35                  40                  45

Pro Ile Leu Met Glu Lys Leu Asn Arg Asn Ser Arg Arg Gly Ile Thr
        50                  55                  60

Tyr Asn Tyr Val Ile Ser Cys Arg Leu Gly Arg Asn Thr Tyr Lys Glu
65                  70                  75                  80

Gln Tyr Ala Phe Leu Tyr Lys Glu Lys Leu Val Ser Val Lys Arg Ser
                85                  90                  95

Tyr His Tyr His Asp Tyr Gln Asp Gly Asp Ala Asp Val Phe Ser Arg
            100                 105                 110

Glu Pro Phe Val Val Trp Phe Gln Ser Pro His Thr Ala Val Lys Asp
            115                 120                 125

Phe Val Ile Ile Pro Leu His Thr Thr Pro Glu Thr Ser Val Lys Glu
        130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
                165                 170                 175

Val Pro Lys Lys Ala Trp Lys Asn Ile Arg Leu Arg Thr Asp Pro Arg
            180                 185                 190

Phe Val Trp Leu Ile Gly Asp Gln Glu Asp Thr Thr Val Lys Lys Ser
            195                 200                 205

Thr Asn Cys Ala Tyr Asp Arg Ile Val Leu Arg Gly Gln Glu Ile Val
        210                 215                 220

Ser Ser Val Val Pro Lys Ser Asn Ser Val Phe Asp Phe Gln Lys Ala
225                 230                 235                 240

Tyr Lys Leu Thr Glu Glu Glu Ala Leu Asp Val Ser Asp His Phe Pro
                245                 250                 255

Val Glu Phe Lys Leu Gln Ser Ser Arg Ala Phe Thr Asn Ser Lys Lys
            260                 265                 270

Ser Val Thr Leu Arg Lys Lys Thr Lys Ser Lys Arg Ser
        275                 280                 285
```

```
<210> SEQ ID NO 3
<211> LENGTH: 285
<212> TYPE: PRT
<213> ORGANISM: Artificial Sequence
<220> FEATURE:
<223> OTHER INFORMATION: Synthetic peptide

<400> SEQUENCE: 3
```

```
Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
            35                  40                  45

Pro Ile Leu Met Glu Lys Leu Asn Arg Asn Ser Arg Arg Gly Ile Thr
        50                  55                  60

Tyr Asn Tyr Val Ile Ser Ser Arg Leu Gly Arg Asn Thr Tyr Lys Glu
65                  70                  75                  80

Gln Tyr Ala Phe Leu Tyr Lys Glu Lys Leu Val Cys Val Lys Arg Ser
                85                  90                  95
```

-continued

```
Tyr His Tyr His Asp Tyr Gln Asp Gly Asp Ala Asp Val Phe Ser Arg
            100             105             110

Glu Pro Phe Val Val Trp Phe Gln Ser Pro His Thr Ala Val Lys Asp
            115             120             125

Phe Val Ile Ile Pro Leu His Thr Thr Pro Glu Thr Ser Val Lys Glu
            130             135             140

Ile Asp Glu Leu Val Glu Val Tyr Thr Asp Val Lys His Arg Trp Lys
145             150             155             160

Ala Glu Asn Phe Ile Phe Met Gly Asp Phe Asn Ala Gly Cys Ser Tyr
                165             170             175

Val Pro Lys Lys Ala Trp Lys Asn Ile Arg Leu Arg Thr Asp Pro Arg
            180             185             190

Phe Val Trp Leu Ile Gly Asp Gln Glu Asp Thr Thr Val Lys Lys Ser
            195             200             205

Thr Asn Cys Ala Tyr Asp Arg Ile Val Leu Arg Gly Gln Glu Ile Val
        210             215             220

Ser Ser Val Val Pro Lys Ser Asn Ser Val Phe Asp Phe Gln Lys Ala
225             230             235             240

Tyr Lys Leu Thr Glu Glu Glu Ala Leu Asp Val Ser Asp His Phe Pro
            245             250             255

Val Glu Phe Lys Leu Gln Ser Ser Arg Ala Phe Thr Asn Ser Lys Lys
            260             265             270

Ser Val Thr Leu Arg Lys Lys Thr Lys Ser Lys Arg Ser
            275             280             285
```

```
<210> SEQ ID NO 4
<211> LENGTH: 285
<212> TYPE: PRT
<213> ORGANISM: Artificial Sequence
<220> FEATURE:
<223> OTHER INFORMATION: Synthetic peptide

<400> SEQUENCE: 4
```

```
Met Arg Ile Cys Ser Phe Asn Val Arg Ser Phe Gly Glu Ser Lys Gln
1               5               10              15

Glu Asp Lys Asn Ala Met Asp Val Ile Val Lys Val Ile Lys Arg Cys
            20              25              30

Asp Ile Ile Leu Val Met Glu Ile Lys Asp Ser Asn Asn Arg Ile Cys
            35              40              45

Pro Ile Leu Met Glu Lys Leu Asn Arg Asn Ser Arg Arg Gly Ile Thr
        50              55              60

Tyr Asn Tyr Val Ile Ser Ser Arg Leu Gly Arg Asn Thr Tyr Lys Glu
65              70              75              80

Gln Tyr Ala Phe Leu Tyr Lys Glu Lys Leu Val Ser Val Lys Arg Ser
                85              90              95

Tyr His Tyr His Asp Tyr Gln Asp Gly Asp Ala Asp Val Phe Ser Arg
            100             105             110

Glu Pro Phe Val Val Trp Phe Gln Ser Pro His Thr Ala Val Lys Asp
            115             120             125

Phe Val Ile Ile Pro Leu His Thr Thr Pro Glu Thr Ser Val Lys Glu
            130             135             140

Ile Asp Glu Leu Val Glu Val Tyr Thr Asp Val Lys His Arg Trp Lys
145             150             155             160

Ala Glu Asn Phe Ile Phe Met Gly Asp Phe Asn Ala Gly Cys Ser Tyr
                165             170             175
```

-continued

```
Val Pro Lys Lys Ala Trp Lys Asn Ile Arg Leu Arg Thr Asp Pro Arg
            180             185             190

Phe Val Trp Leu Ile Gly Asp Gln Glu Asp Thr Thr Val Lys Lys Ser
            195             200             205

Thr Asn Cys Ala Tyr Asp Arg Ile Val Leu Arg Gly Gln Glu Ile Val
            210             215             220

Ser Ser Val Val Pro Lys Ser Asn Cys Val Phe Asp Phe Gln Lys Ala
225             230             235             240

Tyr Lys Leu Thr Glu Glu Glu Ala Leu Asp Val Ser Asp His Phe Pro
            245             250             255

Val Glu Phe Lys Leu Gln Ser Ser Arg Ala Phe Thr Asn Ser Lys Lys
            260             265             270

Ser Val Thr Leu Arg Lys Lys Thr Lys Ser Lys Arg Ser
            275             280             285
```

```
<210> SEQ ID NO 5
<211> LENGTH: 285
<212> TYPE: PRT
<213> ORGANISM: Artificial Sequence
<220> FEATURE:
<223> OTHER INFORMATION: Synthetic peptide

<400> SEQUENCE: 5
```

```
Met Arg Ile Cys Ser Phe Asn Val Arg Ser Phe Gly Glu Ser Lys Gln
1               5               10              15

Glu Asp Lys Asn Ala Met Asp Val Ile Val Lys Val Ile Lys Arg Cys
            20              25              30

Asp Ile Ile Leu Val Met Glu Ile Lys Asp Ser Asn Asn Arg Ile Cys
            35              40              45

Pro Ile Leu Met Glu Lys Leu Asn Arg Asn Ser Arg Arg Gly Ile Thr
            50              55              60

Tyr Asn Tyr Val Ile Ser Cys Arg Leu Gly Arg Asn Thr Tyr Lys Glu
65              70              75              80

Gln Tyr Ala Phe Leu Tyr Lys Glu Lys Leu Val Cys Val Lys Arg Ser
            85              90              95

Tyr His Tyr His Asp Tyr Gln Asp Gly Asp Ala Asp Val Phe Ser Arg
            100             105             110

Glu Pro Phe Val Val Trp Phe Gln Ser Pro His Thr Ala Val Lys Asp
            115             120             125

Phe Val Ile Ile Pro Leu His Thr Thr Pro Glu Thr Ser Val Lys Glu
            130             135             140

Ile Asp Glu Leu Val Glu Val Tyr Thr Asp Val Lys His Arg Trp Lys
145             150             155             160

Ala Glu Asn Phe Ile Phe Met Gly Asp Phe Asn Ala Gly Cys Ser Tyr
            165             170             175

Val Pro Lys Lys Ala Trp Lys Asn Ile Arg Leu Arg Thr Asp Pro Arg
            180             185             190

Phe Val Trp Leu Ile Gly Asp Gln Glu Asp Thr Thr Val Lys Lys Ser
            195             200             205

Thr Asn Cys Ala Tyr Asp Arg Ile Val Leu Arg Gly Gln Glu Ile Val
            210             215             220

Ser Ser Val Val Pro Lys Ser Asn Ser Val Phe Asp Phe Gln Lys Ala
225             230             235             240

Tyr Lys Leu Thr Glu Glu Glu Ala Leu Asp Val Ser Asp His Phe Pro
            245             250             255
```

-continued

```
Val Glu Phe Lys Leu Gln Ser Ser Arg Ala Phe Thr Asn Ser Lys Lys
            260             265                 270

Ser Val Thr Leu Arg Lys Lys Thr Lys Ser Lys Arg Ser
        275             280             285

<210> SEQ ID NO 6
<211> LENGTH: 285
<212> TYPE: PRT
<213> ORGANISM: Artificial Sequence
<220> FEATURE:
<223> OTHER INFORMATION: Synthetic peptide

<400> SEQUENCE: 6

Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
        35                  40                  45

Pro Ile Leu Met Glu Lys Leu Asn Arg Asn Ser Arg Arg Gly Ile Thr
    50                  55                  60

Tyr Asn Tyr Val Ile Ser Cys Arg Leu Gly Arg Asn Thr Tyr Lys Glu
65                  70                  75                  80

Gln Tyr Ala Phe Leu Tyr Lys Glu Lys Leu Val Ser Val Lys Arg Ser
            85                  90                  95

Tyr His Tyr His Asp Tyr Gln Asp Gly Asp Ala Asp Val Phe Ser Arg
            100                 105                 110

Glu Pro Phe Val Val Trp Phe Gln Ser Pro His Thr Ala Val Lys Asp
        115                 120                 125

Phe Val Ile Ile Pro Leu His Thr Thr Pro Glu Thr Ser Val Lys Glu
    130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
            165                 170                 175

Val Pro Lys Lys Ala Trp Lys Asn Ile Arg Leu Arg Thr Asp Pro Arg
            180                 185                 190

Phe Val Trp Leu Ile Gly Asp Gln Glu Asp Thr Thr Val Lys Lys Ser
            195                 200                 205

Thr Asn Cys Ala Tyr Asp Arg Ile Val Leu Arg Gly Gln Glu Ile Val
    210                 215                 220

Ser Ser Val Val Pro Lys Ser Asn Cys Val Phe Asp Phe Gln Lys Ala
225                 230                 235                 240

Tyr Lys Leu Thr Glu Glu Glu Ala Leu Asp Val Ser Asp His Phe Pro
            245                 250                 255

Val Glu Phe Lys Leu Gln Ser Ser Arg Ala Phe Thr Asn Ser Lys Lys
            260             265                 270

Ser Val Thr Leu Arg Lys Lys Thr Lys Ser Lys Arg Ser
        275             280             285

<210> SEQ ID NO 7
<211> LENGTH: 285
<212> TYPE: PRT
<213> ORGANISM: Artificial Sequence
<220> FEATURE:
<223> OTHER INFORMATION: Synthetic peptide

<400> SEQUENCE: 7
```

-continued

```
Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
                20                  25                  30

Asp Ile Ile Leu Val Met Glu Ile Lys Asp Ser Asn Asn Arg Ile Cys
            35                  40                  45

Pro Ile Leu Met Glu Lys Leu Asn Arg Asn Ser Arg Arg Gly Ile Thr
        50                  55                  60

Tyr Asn Tyr Val Ile Ser Ser Arg Leu Gly Arg Asn Thr Tyr Lys Glu
65                  70                  75                  80

Gln Tyr Ala Phe Leu Tyr Lys Glu Lys Leu Val Cys Val Lys Arg Ser
                85                  90                  95

Tyr His Tyr His Asp Tyr Gln Asp Gly Asp Ala Asp Val Phe Ser Arg
            100                 105                 110

Glu Pro Phe Val Val Trp Phe Gln Ser Pro His Thr Ala Val Lys Asp
        115                 120                 125

Phe Val Ile Ile Pro Leu His Thr Thr Pro Glu Thr Ser Val Lys Glu
    130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
                165                 170                 175

Val Pro Lys Lys Ala Trp Lys Asn Ile Arg Leu Arg Thr Asp Pro Arg
            180                 185                 190

Phe Val Trp Leu Ile Gly Asp Gln Glu Asp Thr Thr Val Lys Lys Ser
        195                 200                 205

Thr Asn Cys Ala Tyr Asp Arg Ile Val Leu Arg Gly Gln Glu Ile Val
    210                 215                 220

Ser Ser Val Val Pro Lys Ser Asn Cys Val Phe Asp Phe Gln Lys Ala
225                 230                 235                 240

Tyr Lys Leu Thr Glu Glu Glu Ala Leu Asp Val Ser Asp His Phe Pro
                245                 250                 255

Val Glu Phe Lys Leu Gln Ser Ser Arg Ala Phe Thr Asn Ser Lys Lys
            260                 265                 270

Ser Val Thr Leu Arg Lys Lys Thr Lys Ser Lys Arg Ser
        275                 280                 285
```

<210> SEQ ID NO 8
<211> LENGTH: 285
<212> TYPE: PRT
<213> ORGANISM: Artificial Sequence
<220> FEATURE:
<223> OTHER INFORMATION: Synthetic peptide

<400> SEQUENCE: 8

```
Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
                20                  25                  30

Asp Ile Ile Leu Val Met Glu Ile Lys Asp Ser Asn Asn Arg Ile Cys
            35                  40                  45

Pro Ile Leu Met Glu Lys Leu Asn Arg Asn Ser Arg Arg Gly Ile Thr
        50                  55                  60

Tyr Asn Tyr Val Ile Ser Cys Arg Leu Gly Arg Asn Thr Tyr Lys Glu
65                  70                  75                  80
```

```
Gln Tyr Ala Phe Leu Tyr Lys Glu Lys Leu Val Cys Val Lys Arg Ser
                85                  90                  95

Tyr His Tyr His Asp Tyr Gln Asp Gly Asp Ala Asp Val Phe Ser Arg
                100                 105                 110

Glu Pro Phe Val Val Trp Phe Gln Ser Pro His Thr Ala Val Lys Asp
            115                 120                 125

Phe Val Ile Ile Pro Leu His Thr Thr Pro Glu Thr Ser Val Lys Glu
        130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
                165                 170                 175

Val Pro Lys Lys Ala Trp Lys Asn Ile Arg Leu Arg Thr Asp Pro Arg
            180                 185                 190

Phe Val Trp Leu Ile Gly Asp Gln Glu Asp Thr Thr Val Lys Lys Ser
        195                 200                 205

Thr Asn Cys Ala Tyr Asp Arg Ile Val Leu Arg Gly Gln Glu Ile Val
    210                 215                 220

Ser Ser Val Val Pro Lys Ser Asn Cys Val Phe Asp Phe Gln Lys Ala
225                 230                 235                 240

Tyr Lys Leu Thr Glu Glu Glu Ala Leu Asp Val Ser Asp His Phe Pro
                245                 250                 255

Val Glu Phe Lys Leu Gln Ser Ser Arg Ala Phe Thr Asn Ser Lys Lys
                260                 265                 270

Ser Val Thr Leu Arg Lys Lys Thr Lys Ser Lys Arg Ser
            275                 280                 285

<210> SEQ ID NO 9
<211> LENGTH: 40
<212> TYPE: DNA
<213> ORGANISM: Artificial Sequence
<220> FEATURE:
<223> OTHER INFORMATION: Synthetic primer

<400> SEQUENCE: 9
cgtacaacta tgtgattagc tgtcggcttg gaagaaacac                        40

<210> SEQ ID NO 10
<211> LENGTH: 40
<212> TYPE: DNA
<213> ORGANISM: Artificial Sequence
<220> FEATURE:
<223> OTHER INFORMATION: Synthetic primer

<400> SEQUENCE: 10
gtgtttcttc caagccgaca gctaatcaca tagttgtacg                        40

<210> SEQ ID NO 11
<211> LENGTH: 38
<212> TYPE: DNA
<213> ORGANISM: Artificial Sequence
<220> FEATURE:
<223> OTHER INFORMATION: Synthetic primer

<400> SEQUENCE: 11
ctacaaggaa aagctggtgt gtgtgaagag gagttatc                          38

<210> SEQ ID NO 12
<211> LENGTH: 38
```

-continued

```
<212> TYPE: DNA
<213> ORGANISM: Artificial Sequence
<220> FEATURE:
<223> OTHER INFORMATION: Synthetic primer

<400> SEQUENCE: 12
gataactcct cttcacacac accagctttt ccttgtag                              38

<210> SEQ ID NO 13
<211> LENGTH: 38
<212> TYPE: DNA
<213> ORGANISM: Artificial Sequence
<220> FEATURE:
<223> OTHER INFORMATION: Synthetic primer

<400> SEQUENCE: 13
gttcccaagt caaactgtgt ttttgacttc cagaaagc                              38

<210> SEQ ID NO 14
<211> LENGTH: 38
<212> TYPE: DNA
<213> ORGANISM: Artificial Sequence
<220> FEATURE:
<223> OTHER INFORMATION: Synthetic primer

<400> SEQUENCE: 14
gctttctgga agtcaaaaac acagtttgac ttgggaac                              38
```